US012564450B2

(12) United States Patent
Kaplan et al.

(10) Patent No.: US 12,564,450 B2
(45) Date of Patent: Mar. 3, 2026

(54) CONFIGURABLE SYSTEM AND METHOD FOR INDICATING DEVIATION FROM A MEDICAL DEVICE PLACEMENT PATHWAY

(71) Applicant: Avent, Inc., Alpharetta, GA (US)

(72) Inventors: Hilton M. Kaplan, New York, NY (US); Gabriel P. Artaud, East Windsor, NJ (US); Karl Thomas Bjurbo, Cumming, GA (US); Sung W. Jeon, Johns Creek, GA (US); Shawn G. Purnell, Canton, GA (US); Anthony D. Roberts, Woodstock, GA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 17/519,956

(22) Filed: Nov. 5, 2021

(65) Prior Publication Data

US 2023/0145909 A1 May 11, 2023

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/25* (2016.02); *A61B 90/37* (2016.02); *G01B 7/004* (2013.01); *A61B 2034/2051* (2016.02)

(58) Field of Classification Search
None
See application file for complete search history.

(56) References Cited

U.S. PATENT DOCUMENTS

2003/0163040 A1    8/2003   Gildenberg
2007/0208252 A1    9/2007   Makower
(Continued)

FOREIGN PATENT DOCUMENTS

WO    WO 2021/062373 A2    4/2021
WO    WO 2021/138096 A1    7/2021

OTHER PUBLICATIONS

International Search Report and Written Opinion for PCT/US2022/048372, dated Feb. 21, 2023, 14 pages.

*Primary Examiner* — Christopher Koharski
*Assistant Examiner* — Renee C Langhals
(74) *Attorney, Agent, or Firm* — Meunier Carlin & Curfman LLC

(57) ABSTRACT

A configurable pathway deviation indication system for medical device placement includes one or more user-adjustable pathway boundaries and an indication activated upon reaching or breaching of any of the pathway boundaries. The system may include a medical device configured to be inserted into a patient; a location transmitter configured to transmit a signal related to a position of the medical device; and a detector device configured to receive information related to the patient's body and the location transmitter. The system may be operatively coupled to the location transmitter and the at least one detector device. The system may further include a display and a computing system comprising one or more processors and or more non-transitory computer-readable media. The system can display the position of the location transmitter; determine if the position of the location transmitter reaches any pathway boundaries; and provide the indication when the pathway boundary is breached and/or approached.

21 Claims, 8 Drawing Sheets

(51) Int. Cl.
    *A61B 90/00*        (2016.01)
    *G01B 7/004*        (2006.01)

(56)              References Cited

U.S. PATENT DOCUMENTS

| | | | |
|---|---|---|---|
| 2010/0097373 A1* | 4/2010 | Besz | A61B 5/06 |
| | | | 345/419 |
| 2010/0312095 A1* | 12/2010 | Jenkins | A61B 5/415 |
| | | | 600/411 |
| 2013/0345718 A1* | 12/2013 | Crawford | A61B 5/061 |
| | | | 606/130 |
| 2016/0022374 A1* | 1/2016 | Haider | A61B 17/142 |
| | | | 606/96 |
| 2016/0074123 A1* | 3/2016 | Bly | A61B 34/76 |
| | | | 600/424 |
| 2018/0368930 A1* | 12/2018 | Esterberg | A61B 34/76 |
| 2019/0380787 A1* | 12/2019 | Ye | A61B 1/00149 |
| 2021/0030497 A1* | 2/2021 | Daley | A61B 90/361 |
| 2021/0196312 A1* | 7/2021 | Plewe | A61B 17/3478 |
| 2022/0134558 A1* | 5/2022 | Danilchenko | A61B 34/20 |
| | | | 700/254 |
| 2022/0338938 A1* | 10/2022 | Walen | A61B 17/1628 |

\* cited by examiner

CONFIGURABLE SYSTEM AND METHOD FOR INDICATING DEVIATION FROM A MEDICAL DEVICE PLACEMENT PATHWAY

FIELD OF THE INVENTION

The subject matter of the present invention relates generally to a configurable system and method for indicating deviation from a medical device placement pathway.

BACKGROUND

Physicians and other health care providers frequently use catheters to treat patients. The known catheters include a tube which is inserted into the human body, with or without the aid of a guidewire or a stiffening stylet within. Certain catheters are inserted through the patient's nose or mouth for treating the gastrointestinal tract. These catheters, sometimes known as enteral catheters, typically include feeding tubes. The feeding tube lies in the stomach or intestines, and allow for the delivery of liquid nutrients, liquid medicines or a combination of the two to the patient; or for sampling from or decompressing the gastrointestinal tract (GIT) by allowing for passive or active drainage of contents (gas or liquid media).

Other types of catheters are inserted into the patient's veins or arteries for treating the cardiovascular system. These intravascular catheters include, among others, central venous catheters, peripheral venous catheters and the peripherally inserted central catheters. These catheters include a relatively small tube that passes through the patient's veins or arteries. Depending on the application, the health care provider can use an intravascular catheter to remove blood vessel blockages, place inserts into blood vessels and provide patients with injections of medications, drugs, fluids, nutrients, or blood products over a period of time, sometimes several weeks or more.

Catheters and larger tubes are used in other areas of the body too, for example, tubes in the trachea (Endotracheal Tubes) used to ventilate patients; urinary catheters (via the urethra or by a suprapubic vesicostomy procedure); wound drainage catheters; cerebrospinal fluid shunts; and the like.

When using any such catheters, it is important to place the end of the catheter at the proper location within the human body. Erroneous placement of the catheter tip may injure or harm the patient. For example, if the health care provider erroneously places an enteral catheter into the patient's lungs, this may damage or irritate the lungs, or liquid may be introduced into the lungs with harmful results. If the health care provider erroneously places an intravascular catheter into the wrong blood vessel of the cardiovascular system, the patient may experience injury or a harmful blockages or emboli.

With feeding tubes in particular, it is also prudent to check that the exit aperture of the feeding tube (typically located at or near to the distal end/tip of the tube) remains in its desired location over the period of treatment, e.g., feeding. Protocols that address this requirement in enteral feeding tubes include position verification by X-Ray or monitoring for the appropriate pH of fluids extracted from the feeding tube when not carrying nutritional liquids and careful patient monitoring to ensure nutritional uptake is as expected.

In some cases, health care providers use X-ray machines to gather information about the location of catheters within the body. There are several disadvantages with using X-ray machines. For example, these machines are relatively large and heavy, not always readily available, and are difficult to transport. This often leads to delays in initiating feeding if waiting for confirmation, which can be critical in malnourished infants for example. They also expose the patient to a relatively high degree of X-ray radiation and consume a relatively large amount of energy. These machines are typically not readily accessible for use because, due to their size, they are usually installed in a special X-ray room. This room can be far away from the patient's room. Therefore, health care providers can find it inconvenient to use these machines for performing catheter insertion procedures. Furthermore, it can be inconvenient to transport these machines to a patient's bedside, and they cannot be used at the patient's home for home care catheter procedures. Moreover, even X-rays are not necessarily conclusive as to the location of the catheter tip, as they are often misread by the ward staff rather than waiting for interpretation by a radiologist, and the natural and continuous movement of the internal organs can make it difficult for the physician interpreting the X-ray to be sure of the actual location of the distal end of the catheter.

Another existing catheter locating means involves using an electromagnetic coil positioned inside the catheter and an electromagnetic coil locating receiver outside of the patient's body. One or both such components are powered. The electromagnetic coil is generally incorporated into a stylet or guide wire which is inserted within the catheter. The coil locating receiver can be used to determine the distance the coil is from the receiver and its depth in the patient's body and can communicate with a display to show a reference image of a non-subject body and an image of the electromagnetic coil location and movement over time on the display with the reference image. However, these systems also have several disadvantages. For example, the coil locating receiver is a large device that must rest in a precise location outside the patient's body and does not permit for adjustments due to each individual patient's anatomical size or shape. Furthermore, health care providers can estimate the positioning of the catheter using the electromagnetic coil and coil locating receiver but cannot estimate or view the specific patient's anatomy.

During placement of tubes into the body their positions and pathway may be tracked in real time using electromagnetic or other tracking techniques, as described above. Such tubes may be placed into the GIT for feeding or the trachea for ventilation, as examples. For example, when considering feeding tubes that are designed to enter the esophagus, these may inadvertently enter the airway during placement, potentially causing significant morbidity (injuries may include pneumothorax (air leaking into and accumulating in the pleural space, i.e., between the lung and the chest wall), hemothorax (blood accumulating in the plural space), empyema (pus in the pleural space), pneumonia, aspiration, asphyxiation and potential death, amongst others). Electromagnetic tracking devices such as the CORTRAK* enteral access system (EAS) allow a clinician to visualize any pathway deviations from those expected. For example, a sharp turn to the left or the right when the tube tip is within the chest would indicate airway entry has occurred. The sooner this is recognized, and the tube is withdrawn, the more unlikely that any damage to the airways will occur. If the user does not recognize the deviation (e.g., if it is gentle initially, or they may be looking at the patient or away from the screen), the airway and lungs can be injured severely or even fed into and so "drowning" or infecting that portion of the lungs.

Consequently, there is a need for a pathway deviation indicator to ensure more accurate catheter placement within a predetermined zone. In particular, a pathway deviation indicator that can be configurable by a user to define pathway boundaries would also be useful.

SUMMARY

Objects and advantages of the invention will be set forth in part in the following description, or may be obvious from the description, or may be learned through practice of the invention.

The present invention is directed to a medical device placement configurable pathway deviation indication system. The system includes a medical device comprising a proximal end and a distal end, wherein the distal end is configured to be inserted into a body of a patient; a location transmitter configured to transmit a signal related to a position of the distal end of the medical device; at least one detector device configured to receive information related to the patient's body and the location transmitter; and a configurable pathway deviation indication system operatively coupled to the location transmitter and the at least one detector device. The configurable pathway deviation indication system includes: a display, and a computing system comprising one or more processors and or more non-transitory computer-readable media that collectively store instructions that, when executed by the one or more processors, cause the computing system to perform operations. The operations include: providing a representation of anatomical landmarks of the patient's body; providing one or more pathway boundaries relative to a desired pathway in the representation of the anatomical landmarks; displaying, on the display, the position of the location transmitter of the medical device relative to the desired pathway; determining in real-time if the position of the location transmitter of the medical device approaches, reaches, and/or breaches any of the one or more pathway boundaries; and providing an indication when the location transmitter of the medical device approaches, reaches, and/or breaches any of the one or more pathway boundaries.

In one particular embodiment, the one or more boundaries can include at least one lateral boundary that is parallel to the desired pathway. Further, the at least one lateral boundary can include a left lateral boundary and/or a right lateral boundary, wherein each of the left lateral boundary and the right lateral boundary can be parallel to the desired pathway.

In another embodiment, the one or more boundaries can include a trajectory angle boundary of deviation from the desired pathway.

In an additional embodiment, each of the one or more boundaries can include a predefined maximum limit relative to the desired pathway, further wherein each of the one or more boundaries can include a user-defined adjustable limit that is less than the predefined maximum limit. Moreover, the one or more boundaries can include a default limit that is less than the predefined maximum limit.

In a further embodiment, the indication can be a visual indicator displayed on the display, an audible cue, and/or a haptic cue. Moreover, the visual indicator can include a graphic symbol and/or a change in a visual display of the one or more catheter placement pathway boundaries that has been approached, reached, and/or breached.

In yet another embodiment, a magnitude, frequency, shape, color, and/or pattern of the alert indication can increase or decrease.

In one more embodiment, the pathway deviation indication system can further include an input operatively coupled to the processor, wherein the input can be configured to enable a user to adjust the one or more pathway boundaries.

The present invention is further directed to a computer-implemented method for indicating deviation from a pathway during a medical device placement procedure. The method includes steps of: providing a representation of anatomical landmarks of a patient's body based on information received from at least one detector device; providing one or more pathway boundaries relative to a desired pathway in the representation of the anatomical landmarks; determining a position of a location transmitter of a medical device relative to the at least one detector device using information received from the detector device; displaying, on the display, the position of the location transmitter of the medical device relative to the desired pathway; determining if the position of the location transmitter of the medical device approaches, reaches, and/or breaches any of the one or more pathway boundaries; and providing an indication when the location transmitter of the medical device breaches and/or reaches and/or approaches any of the one or more pathway boundaries.

In one particular embodiment, the step of determining the position of the location transmitter relative to the at least one detector device can be conducted in real-time.

In another embodiment, the step of determining if the position of the location transmitter of the medical device approaches, reaches, and/or breaches any of the one or more pathway boundaries can be conducted in real-time.

In an additional embodiment, the method can further include a step of adjusting the one or more pathway boundaries using an input.

In yet another embodiment, the one or more boundaries can include at least one lateral boundary that is parallel to the desired pathway. Further, the at least one lateral boundary can include a left lateral boundary and/or a right lateral boundary, wherein each of the left lateral boundary and/or the right lateral boundary are parallel to the desired pathway.

In a further embodiment, the one or more boundaries can include a trajectory angle boundary of deviation from the desired pathway.

In still another embodiment, the step of providing an indication can include displaying a visual indicator on the display, initiating an audible cue, and/or generating a haptic cue. Further, a magnitude and/or frequency of the indication can increase or decrease.

In one more embodiment, the method can further include steps of: establishing a maximum pathway boundary; and establishing a default initial pathway boundary.

These and other features, aspects, and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which.

DETAILED DESCRIPTION

Figure 1:
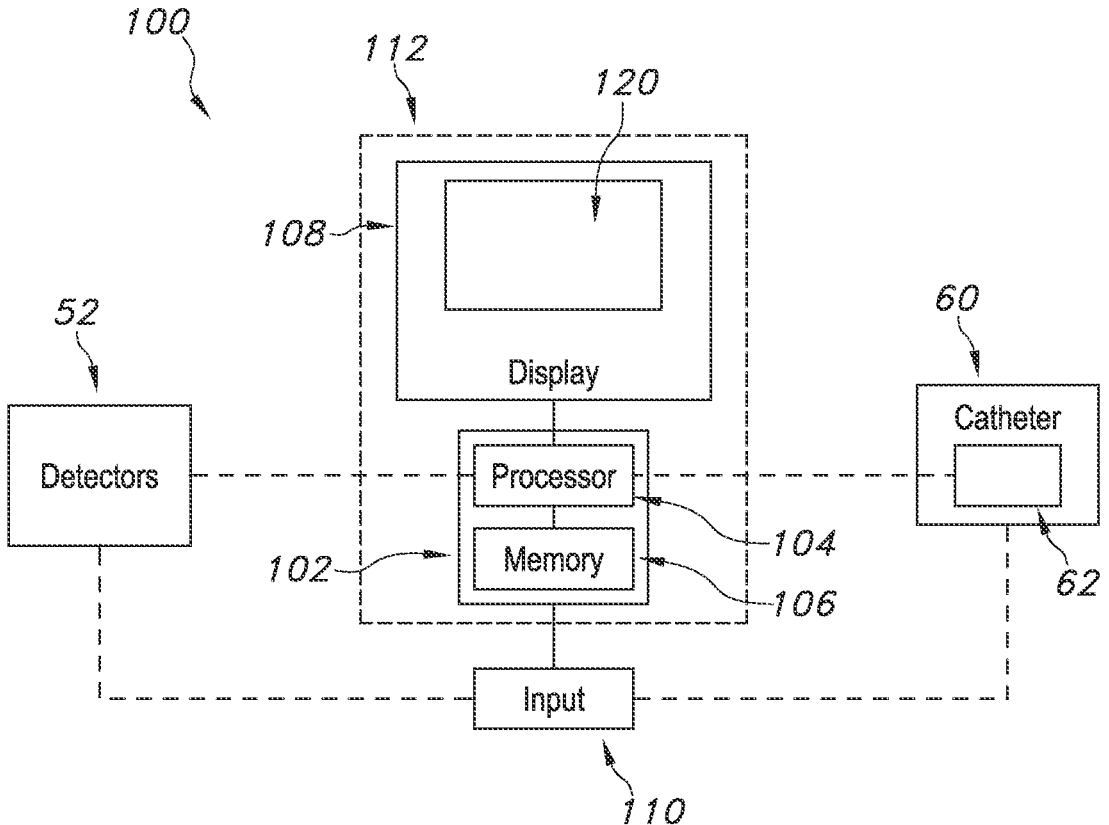
FIG. 1 illustrates a block diagram of a catheter placement pathway deviation indication system according to one particular embodiment of the present invention.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

In the following specification and the claims, reference will be made to a number of terms, which shall be defined to have the following meanings:

The singular forms "a", "an", and "the" include plural references unless the context clearly dictates otherwise.

Approximating language, as used herein throughout the specification and claims, may be applied to modify any quantitative representation that could permissibly vary without resulting in a change in the basic function to which it is related. Accordingly, a value modified by a term or terms, such as "about," "substantially," and "approximately," are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise. Approximating language, when used to modify a value, indicates that the value can be raised or lowered by 10% and remain within the disclosed embodiment, and by as much as 20% when considering anatomical variabilities and remain within the disclosed embodiment. Further, when a plurality of ranges are provided, any combination of a minimum value and a maximum value described in the plurality of ranges are contemplated by the present invention. For example, if ranges of "from about 20% to about 80%" and "from about 30% to about 70%" are described, a range of "from about 20% to about 70%" or a range of "from about 30% to about 80%" are also contemplated by the present invention.

As used herein, the terms "processor" and "computer," and related terms, e.g., "processing device," "computing device," and "controller" are not limited to just those integrated circuits referred to in the art as a computer, but broadly refers to a microcontroller, a microcomputer, a programmable logic controller (PLC), and application specific integrated circuit, and other programmable circuits, and these terms are used interchangeably herein. In the embodiments described herein, memory may include, but it not limited to, a computer-readable medium, such as a random-access memory (RAM), or a computer-readable non-volatile medium, such as a flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner, foot-pedal, headset, or the like. Furthermore, in the exemplary embodiment, additional output channels may include, but not be limited to, an operator interface monitor.

Further, as used herein, the terms "software" and "firmware" are interchangeable and include any computer program storage in memory for execution by personal computers, workstations, clients, and servers.

As used herein, the term "non-transitory computer-readable media" is intended to be representative of any tangible computer-based device implemented in any method of technology for short-term and long-term storage of information, such as, computer-readable instructions, data structures, program modules and sub-modules, or other data in any device. Therefore, the methods described herein may be encoded as executable instructions embodied in a tangible, non-transitory, computer-readable medium, including, without limitation, a storage device and/or a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including without limitation, volatile and non-volatile media, and removable and non-removable media such as firmware, physical and virtual storage, CD-ROMS, DVDs, and any other digital source such as a network or the Internet, as well as yet to be developed digital means, with the sole exception being transitory, propagating signal.

Furthermore, as used herein, the term "real-time" refers to at least one of the time of occurrence of the associated events, the time of measurement and collection of predetermined data, the time to process the data, and the time of a system response to the events and the environment. In the embodiments described herein, these activities and events occur substantially instantaneously.

Generally speaking, the present invention is directed to a medical device placement pathway deviation indication system that is configurable. The system can include a medical device comprising a proximal end and a distal end, wherein the distal end is configured to be inserted into a body cavity of a patient; a location transmitter configured to transmit a signal related to a position of the distal end of the medical device; and at least one detector device configured to receive information related to the patient's body and the location transmitter. The internal component device may generate the signal for detection by the external component device, or vice versa. The system further includes a configurable pathway deviation indication system operatively coupled to the location transmitter and the at least one detector device. The pathway deviation indication system includes a display, a computing system comprising one or more processors and or more non-transitory computer-readable media that collectively store instruction that, when executed by the one or more processors, cause the computing system to perform operations. The operations include: registering and providing a representation of anatomical landmarks of the patient's body; providing one or more pathway boundaries relative to the anatomical landmarks; displaying, on the display, the position of the location transmitter of the medical device relative to the desired pathway; determining in real-time if the position of the location transmitter of the medical device breaches any of the one or more pathway boundaries (e.g., perimeter boundaries or trajectory angle boundaries); and providing an indication when the location transmitter of the medical device breaches any of the one or more pathway boundaries. The present invention is further directed to at least one computer-implemented method for indicating deviation from a pathway during a medical device placement procedure. The present inventors have found that the pathway deviation indication system and method of the present invention can provide a configurable, e.g., self-adjustable aid for guidance during a medical device insertion procedure by providing at least one user-defined pathway boundary over the patient's anatomical landmarks and generating an alarm, alert, graphic, or other indication in real-time when the boundary has been breached. The user-customization of the pathway boundaries enables a user to configure the sensitivity of the pathway deviation indication system based on their own level of expertise, comfort, and desired utility of the system, and further enables the pathway boundaries or trajectory angle limit to be adjusted in real-time during the insertion procedure.

The specific features of the configurable pathway deviation indication system of the present invention may be better understood with reference to FIGS. 1-8.

Referring now to the drawings, FIG. 1 illustrates a block diagram of one embodiment of a medical device placement pathway deviation indication system 100. The medical device placement pathway deviation indication system 100 includes (a) a controller 102 which supports a processor 104 and a memory device 106 and can receive information from an input 110; (b) a display device 108, which may optionally be enclosed in a housing 112 with the controller 102 as shown by dashed lines in FIG. 1; (c) one or more non-invasive external detector devices 52 electronically coupled to the controller 102 by a wire, cable, signal data connection, signal carrier or wireless connection; and optionally (d) an invasive medical device, e.g., a catheter, 60 having a location transmitter 62 in communication with the one or more non-invasive external detector devices 52 and operatively coupled to the apparatus which, in turn, is operatively coupled to the controller 102.

Figure 2:
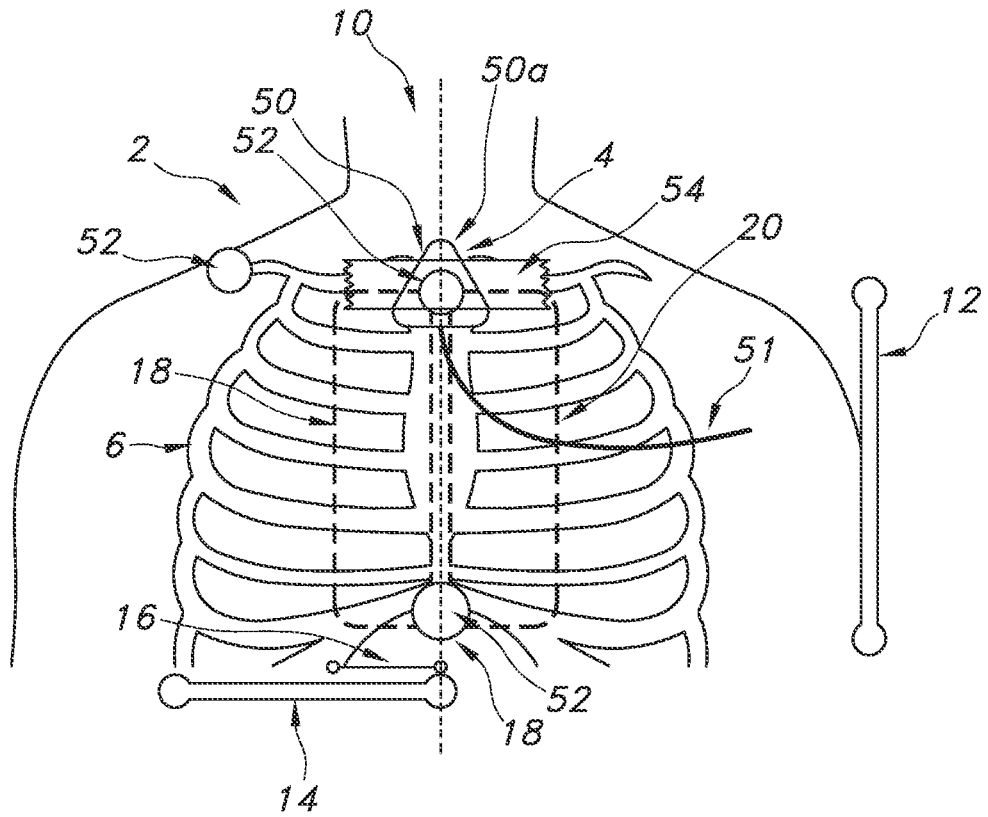
FIG. 2 illustrates a front view of a detector apparatus positioned on a patient's body according to one particular embodiment of the present invention.

As illustrated in FIG. 2, one or more of the non-invasive external detector devices 52 may be disposed in a detector apparatus housing 50. The detector devices 52 may be operatively coupled to the controller 102 via a cable 51 or other wired or wireless connection. Each of the non-invasive external detector devices 52 are configured to be positioned a surface of a subject 2 (see FIG. 2) which is a mammal, such as a human. Although the illustrated example depicts a human, it should be appreciated that medical device placement pathway deviation indication system 100 could be used with any mammals such as domestic animals.

The system 100 of the present invention may rely on "registered" anatomical reference points saved in the memory device 106 of the controller 102. The "registered" anatomical reference points and sizes can be programmed in real-time for each patient's specific anatomy using a registration tool to capture the three-dimensional coordinates of each anatomical landmark in space and store these at the beginning of the tube placement procedure; or may be pre-programmed based on, e.g., average anatomical structure size and relative location of anatomical landmarks such as bony landmarks. Specifically, the memory device 106 can store algorithms defining a generally known pre-defined anthropometric relationship between anatomical landmarks. For instance, an average adult patient, an average pediatric patient of a particular age, etc. The "registered" anatomical reference points may additionally or alternatively be determined by using the non-invasive external detector devices 52 as registration tools, e.g., by positioning the non-invasive external detector devices 52 on known bony landmarks of the patient's body 2 and determining relative distances between each of the non-invasive external detector devices 52. In some aspects of the present invention, a combination of average anatomical size for a patient population and individual patient data received from the non-invasive external detector devices 52 can be used to determine the "registered" anatomical reference points used by the configurable pathway deviation indication system 100.

FIG. 2 further illustrates exemplary anatomical landmarks that may be relevant for placement of an invasive medical device such as a catheter, e.g., enteral feeding tube. The exemplary patient's body 2 may be generally bisected in the frontal plane by midline 10. The midline 10 extends through the suprasternal (jugular) notch 4 of the sternum superiorly and the xiphoid process 8 inferiorly, i.e., the upper and lower landmarks of the sternum. The ribcage is denoted generally by reference numeral 6. A registered height 12 of the chest of the exemplary patient's body 2 may extend along the length between the suprasternal notch 4 and the xiphoid process 8 parallel to the midline 10. A registered width 14 of one side of the chest (a hemithorax) of the exemplary patient 2 may extend generally perpendicular to the midline 10 from the midline to a widest point on the ribcage 6. For placement of an enteral feeding tube, a width 16 relevant to the placement procedure may be defined by about 50% of the registered width 14. A right-side region of interest 18 may be defined as an area formed by the width 16 to the right of the patient's midline and the registered height 12 between the suprasternal notch 4 and the xiphoid process 8. A left-side region of interest 20 may be defined as an area formed by the width 16 to the left of the patient's midline and the registered height 12 between the suprasternal notch 4 and the xiphoid process 8.

The one or more non-invasive external detector devices 52 can be placed on particular bony landmarks of the patient's body 2 to orient and define a coordinate system for determining the location of the invasive medical device 60 within the patient's body 2. For instance, for placement of an invasive medical device such as a catheter, e.g., enteral feeding tube, a detector device 52 can be placed at one or more of the suprasternal notch 4, the xiphoid process 8, and the patient's acromioclavicular joint(s) where the clavicle(s) end in the shoulder joint(s).

The anterior aspect of manubrium of the sternum (the upper bone of the sternum, of which the suprasternal notch 4 is part), appears to be an ideal point on the body for positioning of the detector apparatus 52 by clinicians as it is common to all humans and can be readily located visually or by palpitation regardless of the physical presentation of the patient. However, the use of the suprasternal notch 4 as a bony anatomy landmark is not the only bony point or region of the body that could be used for this purpose. There may be other points of the body to which the measuring equipment can be reliably co-located or located with a predetermined offset, such as over the xiphoid process or acromioclavicular joint(s). Such an arrangement allows the monitor to be used to display a reference point or object, preferably shaped and scaled in proportion with the parts of the body that will be useful to the clinician in the procedure they are performing. Such as when placing a catheter or guide wire or checking the location of a previously located catheter.

In some aspects of the present invention, one or more of the detector devices 52 may be disposed in a housing, e.g., a housing 50*a*. A possible detector apparatus housing shape 50 is also shown in FIG. 2. The shape of the apparatus is of triangular form in plain view and is preferable for its use on the chest of a patient as described previously. This shape is convenient for the clinician to use because its apex 50*a* can be located on the at the suprasternal notch and its longitudinal axis made coincident with the midsagittal line 10 of the patient. However, any suitable shape for housing 50 may be used. The housing 50*a* can be affixed to the patient's body 2 by any suitable means, e.g., using a fixation device 54 such as adhesive tape or a clip interlocking onto an ECG electrode-type pad, to maintain a static point of reference on the patient's body 2. Thus, even when there may be movement of the patient's body 2, a static anatomical reference can be maintained.

The one or more non-invasive external detector devices 52 can use any suitable means to determine relative position and/or distance between each of the devices 52. For instance, in one particular embodiment of the present invention, each of the detector devices 52 can include an electromagnetic transmitter and/or receiver configured to send and/or receive electromagnetic signals between the devices 52, as controlled by the controller 102, to determine the relative position and angular position of each of the detector devices 52. However, the non-invasive external detector devices 52 may further use sound or ultrasound time-of-flight or any other suitable arrangement to determine relative position.

Furthermore, the invasive medical device 60, e.g., catheter, can include a location transmitter 62. For instance, the location transmitter 62 can be disposed at a distal end of the catheter 60. The location transmitter 62 can operatively communicate with one or more detector devices 52 in order to determine the location of the catheter, e.g., the distal end of the catheter 60, relative to the one or more detector devices 52. For instance, in one aspect of the present invention, the location transmitter 62 can be a coil disposed at the distal end of the catheter 60 and operatively coupled to the controller 102, and the coil can generate an electromagnetic signal that can be detected by the detector devices 52, not unlike that described in U.S. Pat. No. 8,265,732, which is hereby incorporated into this specification by reference. The incorporation of the above-mentioned patent does not and should not be construed as an admission of the content of the specification having entered the common general knowledge of those skilled in the art. Moreover, any suitable means can be used to determine a position of the invasive medical device, e.g., the position of the distal end of the catheter 60, relative to the one or more non-invasive external detector devices 52.

Figure 3:
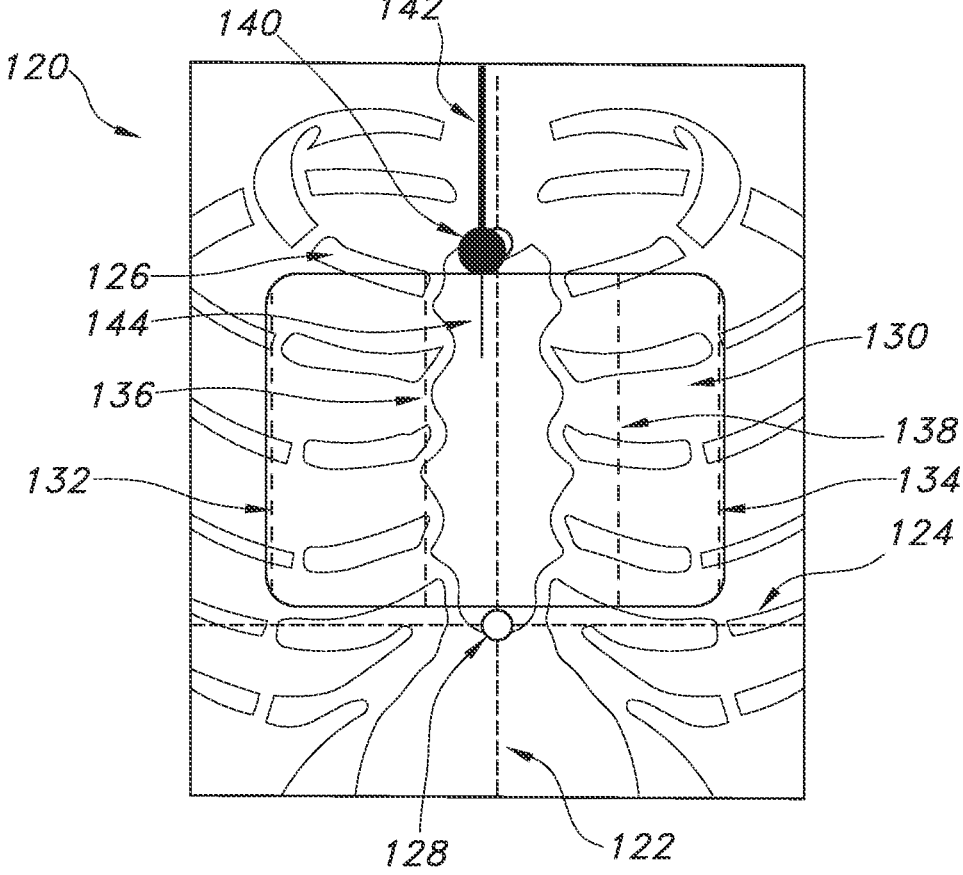
FIG. 3 illustrates an image generated by the system of FIG. 1 according to one embodiment of the present invention.

In use, detector devices 52 can be positioned on or near the patient's body 2 and initiated, e.g., activated or powered on. The processor 104 can receive information related to the relative position between the detector devices 52. The memory device 106 can store image processing algorithms which the processor 104 can execute in order to visually render a graphical representation 126 of a skeletal anatomy scaled appropriately to the patient's torso, e.g., ribcage 6 and depict the rendered graphical representation of the anatomy as an image on a suitable monitor or display 108, e.g., as illustrated in FIG. 3. Further, the memory device 106 can store image processing algorithms which the processor 104 can execute to visually render a graphical representation of the right-side area of interest 18 and the left side area of interest 20, e.g., as an outlined or shaded region overlay as shown in FIG. 3, to illustrate the detection region 22.

The image 120 shown on the display 108 can further include a vertical axis 122 (i.e., a y-axis) that can correspond to the midline 10 of the patient's body 2. Further, the image 120 can include a horizontal axis 124 that is perpendicular to the vertical axis 122 and extends through a graphical representation of the xiphoid process 128 of the patient's body 2 as rendered on the graphical representation of the skeletal anatomy as described above.

The system 100 can further include a right-side "maximum boundary" 132 that extends parallel to a desired pathway for insertion of the medical device 60, e.g., along the vertical axis 122, on the right side of the patient's body, and a left side "maximum boundary" 134 on the left side of the patient's body. The right-side maximum boundary 132 and the left-side maximum boundary 134 may be graphically depicted in the image 120 as vertical lines, e.g., solid lines, or as a visible overlay representing the full detection region 130. The right-side maximum boundary 132 may coincide with the outer right edge of the detection region 130, e.g., at about 50% of the width of the right side of the patient's body 2, otherwise known as the right "hemithorax"; or may be programmed to a portion of the hemithorax width, for e.g., about 50-70% of the hemithorax width during setup before a procedure starts. For instance, the right-side maximum boundary 132 may be a programmed value stored by the memory device 106, or the right-side maximum boundary 132 may be calculated using one or more algorithms stored in the memory device 106 using information received from the detector devices 52, or any combination thereof. Similarly, the left-side maximum boundary 134 may coincide with the outer left edge of the detection region 130, e.g., at about 50% of the width of the left side of the patient's body 2; or may be programmed to a portion of the hemithorax width, for e.g., about 50-70% of the hemithorax width during setup before a procedure starts. For instance, the left-side maximum boundary 134 may be a programmed value stored by the memory device 106, or the left-side maximum boundary 134 may be calculated using one or more algorithms stored in the memory device 106 using information received from the detector devices 52, or any combination thereof.

Further, the system 100 can have "user-adjustable boundaries" set as lateral perimeter boundaries 136 and 138 that fall within the detection region 130 and can be adjustable by the user during use of the system 100. For instance, a right lateral boundary 136 and a left lateral boundary 138 can be established and adjusted by a user as needed within the previously defined detection region 130 (within its maximum boundaries 134 and 132). The right lateral boundary 136 and the left lateral boundary 138 may be graphically depicted in the image 120 as vertical lines, e.g., solid lines or broken lines, parallel to the desired pathway along the vertical axis 122. Each of the right and left lateral boundaries 136 and 138 may be user-adjustable relative to a distance between the desired pathway along the vertical axis 122 and the right and left-side maximum boundaries 132 and 134. For instance, the right and left lateral boundaries 136 and 138 may be set as a percentage of the width from the desired pathway along the vertical axis 122 and the respective right and left-side maximum boundaries 132 and 134, where 0% is along the desired pathway or vertical axis 122 and 100% coincides with the respective right and left-side maximum boundaries 132 and 134. For instance, the right and left lateral boundaries 136 and 138 may be set in a range from 1% to 100%, such as from 5% to 100%, 10% to 100%, or 15% to 100%. The right and left lateral boundaries 136 and 138 may be set independently of each other, or the right and left lateral boundaries 136 and 138 may be set together in sync. This will allow the user to configure the sensitivity of the pathway deviation indicator system 100 to their own level of expertise and/or comfort with the insertion procedure, and the user's desired utility-level for the system 100 (e.g., if the user intends to rely heavily on the boundaries for guidance during the insertion procedure, the respective right and left lateral boundaries 136 and 138 may be relatively narrowly set).

The controller 102 can receive information from input 110 related to the user-adjustable boundaries. For instance, a user can input an initial right lateral boundary 136 and an initial left lateral boundary 138 prior to beginning an insertion procedure. The right lateral boundary 136 and the left lateral boundary 138 can be equal, or they can have different values. Moreover, the user can utilize the input 110 to adjust the right lateral boundary 136 and/or the left lateral boundary 138 in real-time during an insertion procedure. The right and left lateral boundaries 136 and 138 may be set independently by the input 110 and/or equally in sync.

The input 110 can be any suitable input such as a mouse, keyboard, scroll knob, scroll wheel, touch screen (e.g., a touch screen on the display 108 or an independent touch screen), a foot-pedal(s), a wired or wireless device such as a tablet, or any other input device configured to operatively connect with the controller 102.

Using the information gathered from detector device(s) 52 and the location transmitter 62 regarding the relative position and orientation of the catheter tip 64, when the insertion procedure is initiated, the relative position and direction of the catheter tip within the subject can be graphically represented in the image 120 on the display 108. Moreover, in some aspects of the invention, the relative position and orientation data of the catheter tip 64 can indicate the relative positions of the tip 64 in three spatial dimensions: x (transverse across the body 2), y (longitudinal along the body 2) and z (depth within the body 2).

Specifically, the image 120 may illustrate a graphical representation 140 of the relative location of the distal tip 64 of the catheter 60. The graphical representation 140 may be illustrated as a dot, an arrow, an icon, a shape, or any other suitable illustrative representation to indicate a current, real-time relative location (and or trajectory angle) of the distal tip 64 of the catheter 60. Further, the image 120 may use all prior locations to illustrate a graphical representation 142 tracing the catheter's pathway 60 within the patient's body 2. The graphical representation of the catheter tracing 142 can illustrate the position of the pathway of the catheter within the patient's body 2, as shown in FIG. 3. The graphical representation of the catheter tracing 142 can be illustrated, e.g., as a solid, dotted or dashed line in a same color or different color than that of the graphical representation 140 of the position of the distal tip 64 of the catheter 60. Moreover, the graphical representation of the catheter tracing 142 can have a different size/thickness, color, shape, pattern or appearance than the graphical representation of the tip 140. For instance, as shown in FIGS. 3-7, the catheter tracing 142 can have a different graphical representation 140 of the distal tip of the catheter, and the graphical representation 140 of the distal tip of the catheter can have a thickness or width or color or shape that is different from that of the catheter tracing 142. Such differences in size/thickness, color, shape, pattern or appearance, may be used to indicate a change in trajectory angle, depth or any other feature according to the tip's location. However, for the purpose of the present invention, the style of the graphical representation is not critical and any suitable graphical representation for the relative position of the catheter 60 within the patient's body 2 can be used.

During an insertion procedure, the right and left lateral user-adjustable boundaries 136 and 138, respectively, may be shown on the image 120 as described above. As the catheter 60 is inserted into the patient's body 2, the controller 102 can receive the information related to the relative position of the location transmitter 62 and compare to the right and left lateral boundaries 136 and 138 set by the user. If at any point the relative position of the location transmitter 62 approaches, reaches, or breaches the right lateral boundary 136 or the left lateral boundary 138, the user may be notified. Specifically, image 120 may show the graphical representation 140 of the location transmitter and at least a portion of the graphical representation 142 of the catheter tracing nearing, crossing or positioned on the right lateral boundary 136 or the left lateral boundary 138 relative to the desired pathway, e.g., along the vertical axis 122.

As used herein, the term "approach" or "approaching" the user-adjustable boundaries means that the relative position of the location transmitter 62 is within about 0-30% of the distance from a user-adjustable boundary to the desired pathway, e.g., the right lateral boundary 136 or the left lateral boundary 138, within the region between the respective boundary and the desired pathway, e.g., vertical axis 22. In this manner, a pathway deviation indicator 150 can be initiated as a caution alert to warn a user that the relative position of the location transmitter 62 may be nearing a particular user-defined boundary. In some aspects of the invention, the use of a caution alert can be configured by a user, e.g., to define the tolerance between about 0-30% of the distance from the respective boundary to the desired pathway at which the user would like to receive a caution alert. A tolerance of 0% for the caution alert would occur when the relative position of the location transmitter 62 reaches or is touching the respective boundary, e.g., one of the right lateral boundary 136 or the left lateral boundary 138. A tolerance of 30% would provide a pathway deviation indicator 150 as a caution alert when the relative position of the location transmitter 62 is within 30% of the distance, e.g., width, between the respective boundary and the desired pathway. As an illustrative example only, if a distance between the vertical axis 22 and the right lateral boundary 136 is 10 cm, a caution alert can be initiated when the relative position of the location transmitter 62 approaches the right lateral boundary 136 within 3 cm if the caution alert tolerance is 30%.

Furthermore, one or more pathway deviation indicators 150 may be initiated to alert the user of a pathway deviation from, e.g., the relative position of the location transmitter 62 approaching, reaching, or breaching, the lateral user-adjustable boundaries. For instance, a visual warning graphic 152 may pop up on the image 120, the graphical representation 140 of the location transmitter and/or the graphical representation 142 of the catheter tracing may change in size, color, and/or pattern (including but not limited to a flashing graphic), or any other visual alert may be initiated. Additionally or alternatively, the indicators 150 may include audible cues, such as an alert sound, and/or haptic cues, such as a vibration of the input 110 or other apparatus which a user may be in contact with.

The pathway deviation indicators 150 may be of varying and/or progressively changing frequencies or amplitudes. For instance, the colors, shapes, frequencies and/or amplitudes of the indicators 150 may increase or decrease, or the type of indicator 150 may change, if the indicator 150 is ignored by the user. Similarly, the colors, shapes, frequencies and/or amplitude of the indicators 150 may increase or decrease relative to, e.g., proportionally to, the amount or distance beyond the right or left lateral user-adjustable boundaries 136 and 138 that the path of the catheter has deviated. In the instance of a visual warning graphic 152, the visual warning graphic 152 may increase or decrease in size, change color, flash on screen, or any combination thereof if the user does not respond to the indicators 150. Similarly, the frequency and/or amplitude of audible or haptic cues may increase or decrease if the user does not respond to the indicator(s) 150. It may be considered that an indicator 150 is ignored or not responded to by the user if the insertion procedure continues with the location transmitter 62 outside the lateral boundaries 136 or 138 without any course correction to bring the location transmitter 62 back within the lateral boundaries 136 or 138, e.g., by removing some or all of the length of the catheter 60 from the patient's body 2; or by widening the user-adjustable boundaries to abort the alert.

As described above, the right lateral user-adjustable boundary 136 and/or left lateral user-adjustable boundary 138 can be adjusted by the user in real-time. For instance, if the system 100 detects that the location transmitter 62 has reached or crossed the right lateral boundary 136 and generates one or more pathway deviation indicators 150, the user may widen the right lateral boundary 136 in real-time if the user does not believe the actual insertion path of the catheter 60 is in error. When the right lateral boundary 136 is widened in real-time such that the detected position of the location transmitter 62 is now considered to be in-bounds, the pathway deviation indicator(s) 150 may be inactivated or turned off. These adjustments may be made unilaterally, or bilaterally individually, or bilaterally in sync.

In some aspects of the present invention, the processor 104 may further utilize information gathered from detector device(s) 52 and the location transmitter 62 with algorithms stored in the memory device 106 to estimate an angle trajectory of the tip 64 of the catheter 60 within the patient's body 2. A graphical representation 144 of the angle trajectory may be further generated and shown on the image 120, e.g., as an arrow tip or a line extending from the graphical representation 140 of the position of the distal tip 64 of the catheter 60. The graphical representation 144 of the angle trajectory may be visually represented as, e.g., an arrow, a solid line, dashed and/or dotted line, having a different color than one or more of the graphical representation(s) 140 of the distal tip of the catheter and the graphical representation(s) of the catheter tracing 142.

The system 100 may further include a "trajectory angle boundary" which defines the maximum allowable angle of deviation relative to the desired pathway, e.g., along the patient's midline 10, represented by the vertical axis 122 in the image 120 represented on the display 108. During a procedure of insertion of a tube such as an enteral feeding tube, a sharp turn to the left or the right when the tube tip 64 is within the chest would indicate airway entry has occurred. The system 100, in particular, the controller 102, can compare the angle trajectory of the location transmitter 62 within the patient's body 2 with the trajectory angle boundary value which defines a maximum acceptable angle of deviation. When the trajectory angle is greater than the boundary angle of deviation, one or more pathway deviation indicators 150 may be initiated to alert the user of a pathway deviation beyond the boundary angle. The pathway deviation indicators 150 may function the same as described above with regard to touching or breaching the right and left lateral boundaries 136 and 138. For instance, the pathway deviation indicators 150 may increase in frequency and/or amplitude if the boundary angle deviation indicators 150 are ignored. Additionally, the pathway deviation indicators 150 may increase in frequency and/or amplitude based on the amount beyond the boundary angle of deviation 146 that the trajectory angle has deviated.

FIGS. 4-7 will now be discussed in further detail to illustrate the use of the pathway deviation indication system 100 described above.

Figure 4:
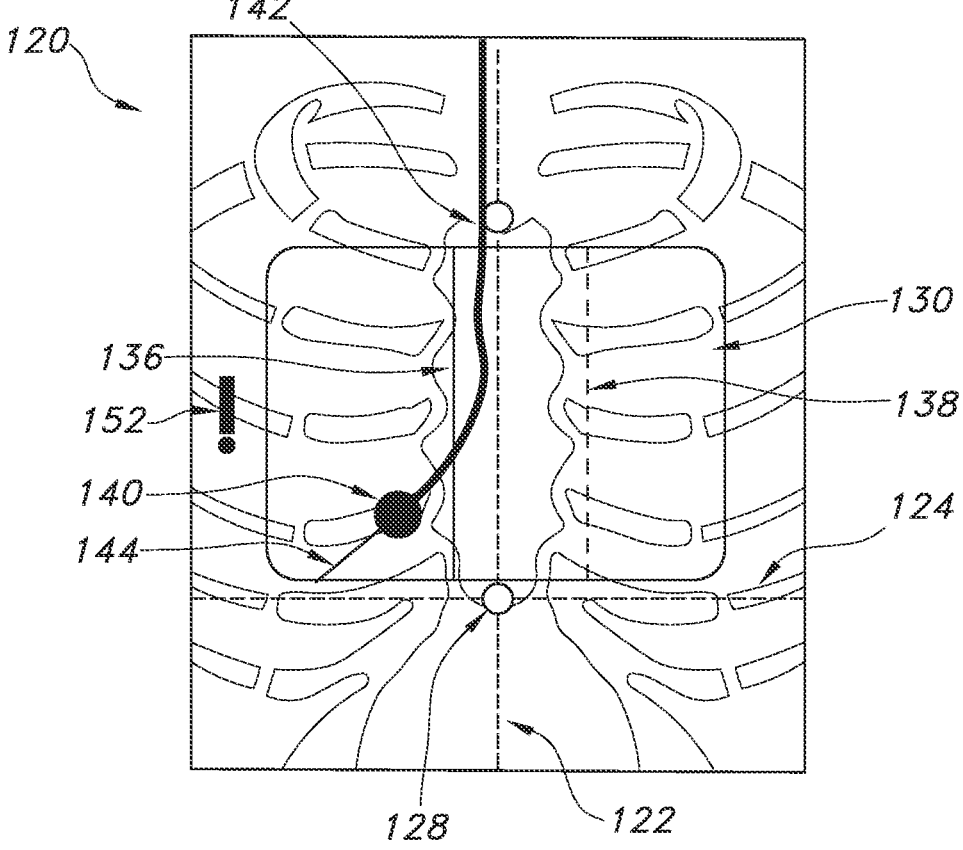
FIG. 4 illustrates an image generated by the system of FIG. 1 according to another aspect of the present invention in which a pathway boundary is breached and an indication is generated.

FIG. 4 shows an image 120 generated by the system 100 in a condition in which the right lateral user-adjustable boundary 136 is narrower than the left lateral user-adjustable boundary 138. The graphical representation 140 of the position of the distal tip 64 of the catheter 60 shows that the right lateral user-adjustable boundary 136 has been breached. Multiple pathway deviation indicators 150 are shown in the image 120. Specifically, the right lateral boundary 136 has changed from a dashed line (e.g., shown in FIG. 3) to a solid line. Further, a visual warning graphic 152 is shown in the image 120.

Figure 5:
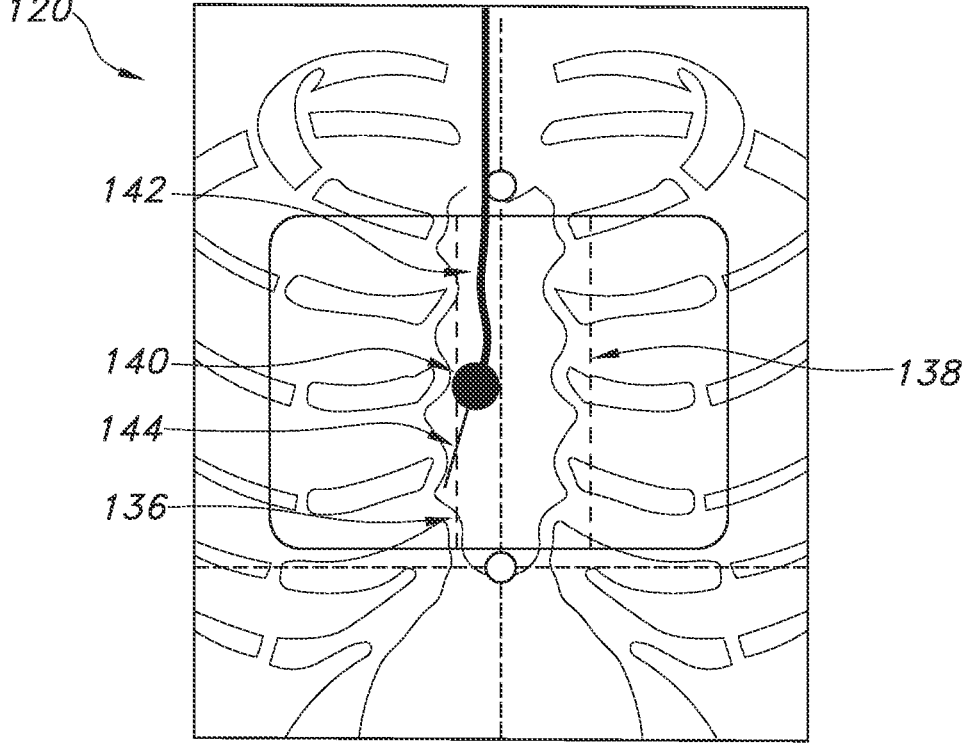
FIG. 5 illustrates an image generated by the system of FIG. 1 according to another aspect of the present invention in which a pathway boundary is not reached or breached and therefore an alert indication is not generated.

FIG. 5 shows an image 120 having a right lateral user-adjustable boundary 136 and left lateral user-adjustable boundary 138 having the same width settings as shown in FIG. 4. However, in FIG. 5, the pathway of the inserted catheter, i.e., the catheter tracing 142 and the distal tip 140 of the catheter as shown on the image 120, remain in-bounds relative to both the right lateral user-adjustable boundary 136 and left lateral user-adjustable boundary 138. The angle trajectory 144 shown in FIG. 5 shows an anticipated pathway that may extend beyond the right lateral boundary 136. Thus, the system 100 may optionally generate one or more pathway deviation indicators 150 which may change progressively as the catheter tip representation 140 approaches the user-adjustable boundary 136.

Figure 6:
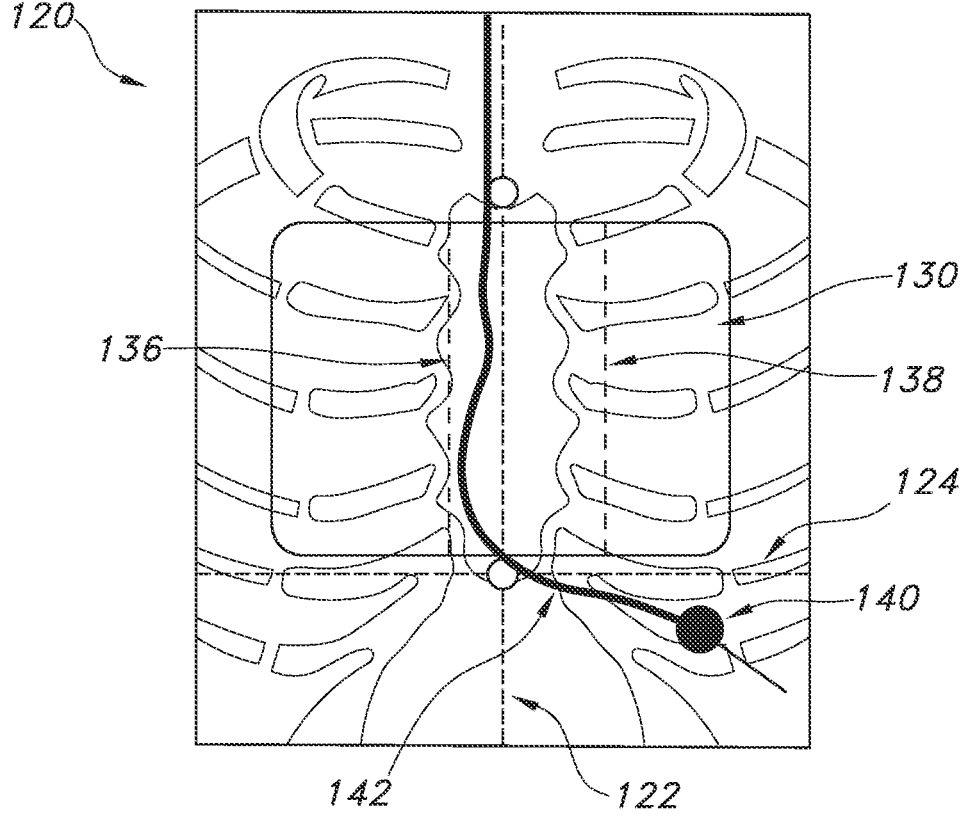
FIG. 6 illustrates an image generated by the system of FIG. 1 according to another aspect of the present invention in which the medical device has passed beyond the scope of the pathway boundary.

FIG. 6 shows an image 120 in which the catheter tracing 142 and the graphical representation 140 of the real-time position of the location transmitter 62 has passed below the horizontal axis 124, i.e., has extended below the patient's anterior chest. The image 120 appears to show that the catheter tracing 142 and the graphical representation 140 of the real-time position of the location transmitter 62 have extended beyond a width coinciding with the left lateral user-adjustable boundary 138. However, in this case, the left lateral boundary 138 has not been reached or breached because the left lateral boundary 138 is not crossed above the horizontal axis 124, i.e., in the patient's chest 2. Thus, no pathway deviation indicators 150 are generated.

Figures 7A, 7B:
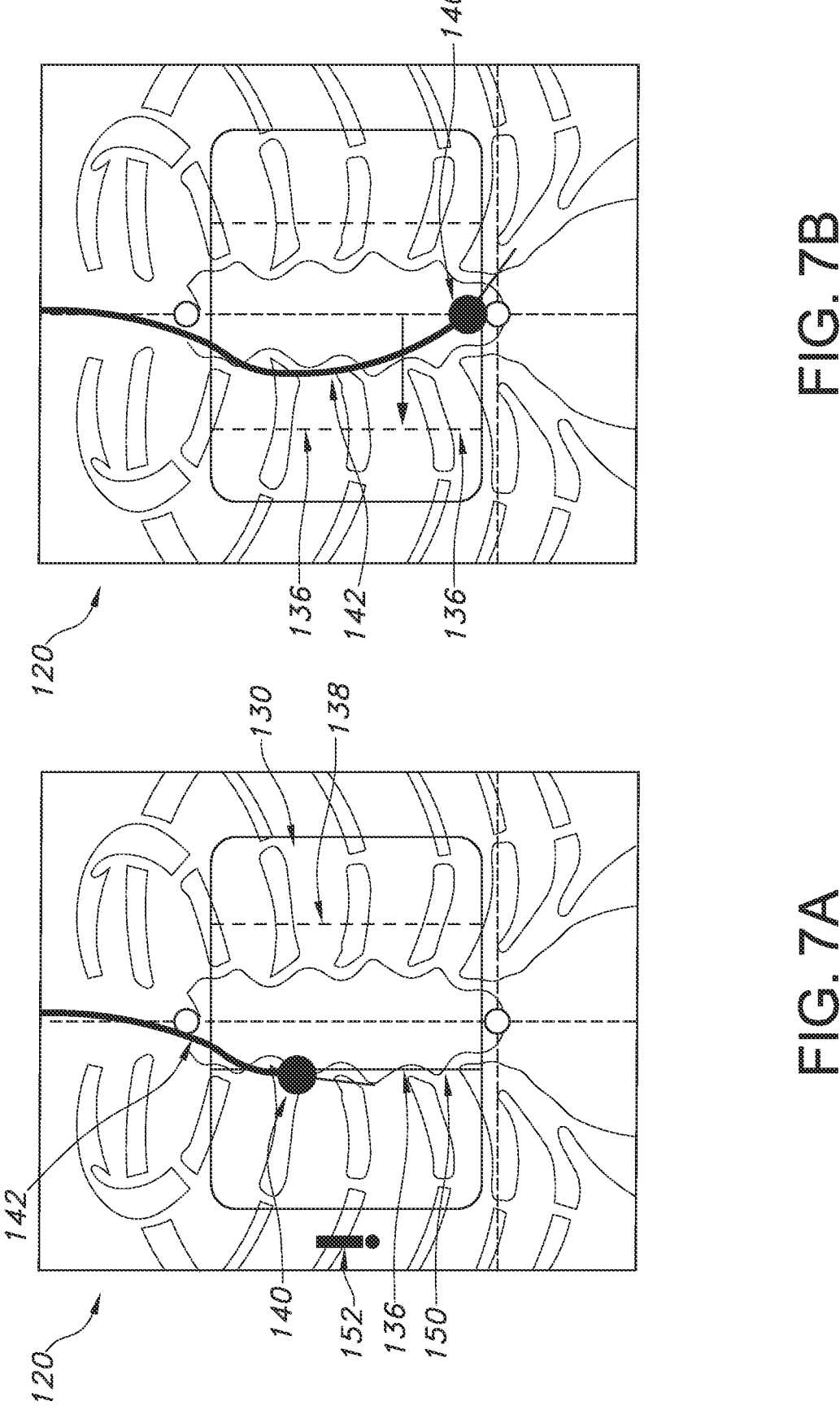
FIGS. 7A and 7B illustrate images generated by the system of FIG. 1 according to another aspect of the present invention when the pathway boundary is user-adjusted in real-time to be less restrictive (by offering wider limits)
Figure 8:
FIG. 8 illustrates a block diagram of a method implemented by the system of claim 1.
Figure 8:
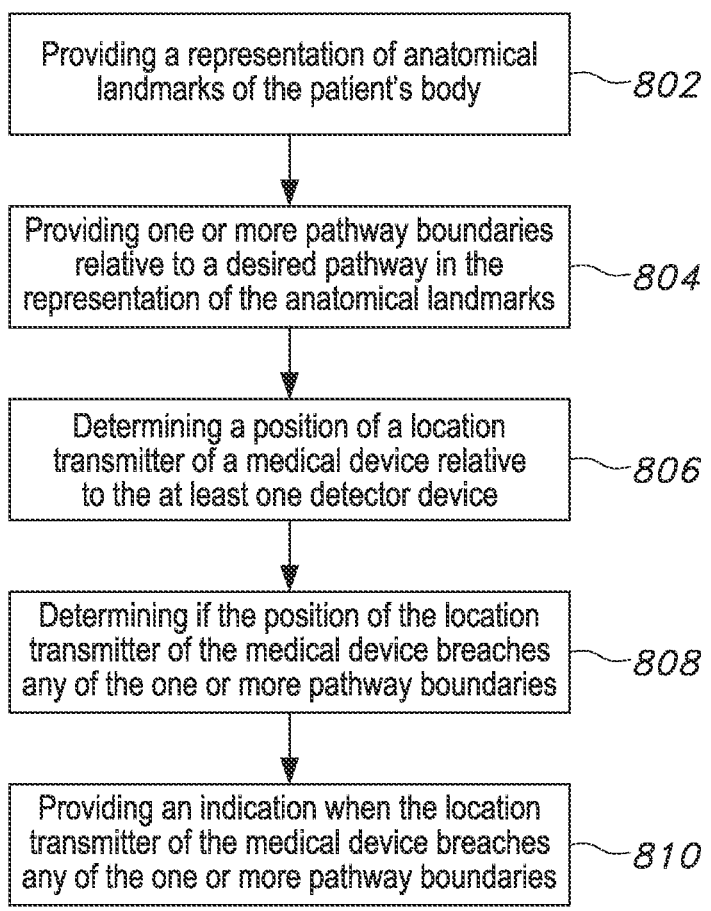

FIGS. 7A and 7B illustrate a scenario in which a user has adjusted the right lateral user-adjustable boundary 136 in real-time during an insertion procedure to make it wider (as seen from FIG. 7A to FIG. 7B). In particular, FIG. 7A illustrates a similar condition to that as shown in FIG. 4 above, in which the right lateral user-adjustable boundary 136 is breached and one or more pathway deviation indicators 150 are activated. FIG. 7B illustrates that the right lateral user-adjustable boundary 136 is widened, i.e., moved laterally away from the desired pathway along the vertical axis 122 and toward the right maximum boundary 132. With the right lateral boundary 136 augmented, the catheter tracing 142 is no longer out-of-bounds, and the pathway deviation indicators 150 can be turned off.

The present invention further contemplates additional mechanisms for setting the lateral boundaries. For instance, the system 100 can be configured to have customer-specific default and/or lateral maximum boundaries, where the customer is, for instance, a healthcare system, hospital, doctor's office, clinician, or other user. If desired, customer-specific maximum boundaries that are less than 100%, i.e., less than the hemithorax width for the right-side maximum boundary 132 and the left-side maximum boundary 134. When customer-specific maximum boundaries are set, the user-adjustable right lateral boundary 136 and the left lateral boundary 138 may not exceed the customer-specific maximum boundaries. These adjustments to the maximum boundaries may be made unilaterally or bilaterally individually or bilaterally in sync, before a procedure begins.

Additionally, the system 100 may be configured with customer-specific default lateral user-adjustable boundaries as well. For instance, a particular customer or user may specify particular default starting points for the right lateral user-adjustable boundary 136 and the left lateral user-adjustable boundary 138, within the limits of the right-side and left-side maximum boundaries 132 and 134. When the user initiates the system 100 during an insertion procedure, the right lateral user-adjustable boundary 136 and the left lateral user-adjustable boundary 138 will initially be positioned at the specified default lateral user-adjustable boundaries. By way of example, one user may set their specific default starting lateral user-adjustable boundaries at 20% of maximum boundary width for the right lateral user-adjustable boundary 136 and at 40% of maximum boundary width for the left lateral user-adjustable boundary 138 (in recognition that tubes in the trachea may pass more easily into the right lung than the left one, due to the more obtuse main bronchus angle on the left-side from the presence of the heart predominantly on that side of the chest).

The present invention may be further directed to a computer-implemented method for indicating deviation from a pathway during a catheter placement. The computer-implemented method may be executed by the processor 104 and the memory device 106, in conjunction with the display 108 and the input 110 described above.

At step 802, the method includes providing a representation of anatomical landmarks of the patient's body based on information received from at least one detector device 52. For instance, an image 120 as described above may be generated including the vertical midline 122 and representation of the xiphoid process 128, among other anatomical landmarks if desired.

Next, at step 804, the method includes providing one or more pathway boundaries relative to a desired pathway, e.g., along the vertical midline 122 in the representation of the anatomical landmarks, e.g., the image 120. For instance, the right and left maximum boundaries 132 and 134 may be displayed on the image 120 as the pathway boundaries. Additionally or alternatively, the right and left pathway user-adjustable boundaries 136 and 138 may be provided on the image 120.

Next, at step 806, the method includes determining a position of a location transmitter of a medical device, e.g., the location transmitter 62, relative to the at least one detector device, e.g., detector devices 52, using information received from the detector device(s) 52.

Next, at step 808, the method includes displaying on the display, e.g., image 120, the position of the location transmitter of the medical device relative to the desired pathway, e.g., along the vertical midline 122 and determining if the position of the location transmitter of the medical device reaches or breaches any of the one or more pathway boundaries. For instance, the image 120 may show if/when the position of the location transmitter 62 crosses one of the right or left pathway user-adjustable boundaries 136 or 138, or if the trajectory 144 of the location transmitter 62 exceeds the angle of the trajectory angle boundary.

Then, at step 810, the method includes providing an indication when the location transmitter of the medical device reaches or breaches any of the one or more pathway boundaries. For instance, the step 810 may include displaying a visual indicator on the display, initiating an audible cue, and/or generating a haptic cue.

The method steps 802-810 can be conducted in real-time, in particular the steps of determining the position of the location transmitter, e.g., transmitter 62, relative to the detector device(s) 52 and the pathway boundaries.

Further, the method can include step(s) of adjusting the one or more pathway boundaries using an input, e.g., the input 110 as described above.

An exemplary technical effect of the methods, systems, and apparatus described herein includes at least one of, but are not limited to: a) improving medical device placement pathway accuracy and efficiency using existing hardware for medical device tracking, and b) reducing the likelihood of patient injury during medical device placement procedures.

Exemplary embodiments of medical device placement tracking systems that are configurable and include pathway deviation indicators are described above in detail. The medical device placement tracking systems, devices, and methods of using such systems and devices are not limited to the specific embodiments described herein, but rather, components of systems and/or steps of the methods may be utilized independently and separately from other components and/or steps described herein. For example, the methods may also be used in combination with other medical device tracking systems and are not limited to practice with only the medical device tracking systems, and methods as described herein. Rather, the exemplary embodiment can be implemented and utilized in connection with many other medical device tracking systems.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims and may include other examples that occur to those skilled in the art. Such other examples are intended to be within the scope of the claims if they include structural elements that do not differ from the literal language of the claims or if they include equivalent structural elements with insubstantial differences from the literal language of the claims.

What is claimed is:

1. A medical device placement configurable pathway deviation indication system comprising:

a catheter comprising a proximal end and a distal end, wherein the distal end is configured to be inserted into a desired catheter pathway within a body cavity of a patient through the patient's nose or mouth;

a location transmitter configured to transmit a signal related to a position of the distal end of the catheter;

at least one detector device configured to be placed on a patient's body for determining anatomical landmarks of the patient's body in real-time, the at least one detector device configured to receive information related to the anatomical landmarks of the patient's body and a position of the location transmitter, wherein the information related to the anatomical landmarks comprises a suprasternal notch and a xiphoid process of the sternum of the patient, wherein the suprasternal notch defines an upper landmark and the xiphoid process defines a lower landmark; and a configurable pathway deviation indication system operatively coupled to the location transmitter and the at least one detector device, the configurable pathway deviation indication system comprising:

a display, a computing system comprising one or more processors and one or more non-transitory computer-readable media that collectively store instructions that, when executed by the one or more processors, cause the computing system to perform operations, the operations comprising:

providing a representation of the anatomical landmarks of the patient's body and providing a detection region based on the anatomical landmarks received from the at least one detector device, the detection region defined between the upper landmark and the lower landmark of the sternum of the patient;

providing one or more lateral pathway boundaries relative to the desired catheter pathway in the representation of the anatomical landmarks, the one or more lateral pathway boundaries positioned within the detection region and extending between the upper landmark and the lower landmark;

displaying, on the display, the position of the location transmitter of the catheter relative to the desired catheter pathway;

determining in real-time if the position of the location transmitter of the catheter approaches, reaches, and/ or breaches any of the one or more lateral pathway boundaries;

determining in real-time if the position of the location transmitter of the catheter is within the detection region;

providing an indication when the location transmitter of the catheter approaches, reaches, and/or breaches any of the one or more lateral pathway boundaries within the detection region; and determining in real-time if the position of the location transmitter of the catheter is outside the detection region and is at a position below the xiphoid process, wherein the location transmitter is configured to extend beyond a width of the one or more lateral pathway boundaries when the catheter is below the xiphoid process, wherein the indication is not provided when the location transmitter of the catheter is outside the detection region at the position below the xiphoid process and approaches, reaches, and/or breaches the width coinciding with any of the one or more lateral pathway boundaries.

2. The system of claim 1, wherein the desired catheter pathway is defined along a midline of the patient, and wherein the one or more lateral pathway boundaries are parallel to the desired catheter pathway.

3. The system of claim 2, wherein the one or more lateral pathway boundaries comprises a left lateral boundary and/or a right lateral boundary, wherein each of the left lateral boundary and the right lateral boundary are parallel to the desired catheter pathway.

4. The system of claim 1, wherein the operations include determining a trajectory angle of the distal end of the catheter within the body cavity of the patient, and wherein the configurable pathway deviation indication system is configured to compare the trajectory angle to a trajectory angle boundary defining a maximum acceptable angle of deviation from the desired catheter pathway.

5. The system of claim 1, wherein each of the one or more lateral pathway boundaries comprises a predefined maximum limit relative to the desired catheter pathway, further wherein each of the one or more lateral pathway boundaries comprises a user-defined adjustable limit that is less than the predefined maximum limit.

6. The system of claim 5, wherein the one or more lateral pathway boundaries comprises a default limit that is less than the predefined maximum limit.

7. The system of claim 1, wherein the indication is a visual indicator displayed on the display, an audible cue, and/or a haptic cue, and wherein the visual indicator comprises a graphic symbol and/or a change in a visual display of the one or more lateral pathway boundaries that has been approached, reached, and/or breached.

8. The system of claim 1, wherein a magnitude, frequency, shape, color, and/or pattern of the indication increases or decreases.

9. The system of claim 1, wherein the pathway deviation indication system further includes an input operatively coupled to the processor, wherein the input is configured to enable a user to adjust the one or more lateral pathway boundaries.

10. The system of claim 1, wherein the desired catheter pathway is configured to allow the catheter to treat the patient's gastrointestinal tract.

11. The system of claim 1, wherein the anatomical landmarks from the at least one detector device is programmed in real-time for the patient's specific body using a registration tool to capture three-dimensional coordinates of the anatomical landmarks, and wherein the detection region is defined on the three-dimensional coordinates of the anatomical landmarks.

12. A computer-implemented method for indicating deviation from a pathway during a catheter placement procedure, the method comprising steps of:

inserting a catheter through a desired catheter pathway into a body cavity of a patient through the patient's nose or mouth;

providing a pair of detector devices on a patient's body;

determining relative distances between each of the detector devices to determine anatomical landmarks of the patient's body in real-time;

providing a representation of the anatomical landmarks of the patient's body based on information received from the pair of detector devices, wherein the information related to the anatomical landmarks comprises a suprasternal notch and a xiphoid process of the sternum of the patient, wherein the suprasternal notch defines an upper landmark and the xiphoid process defines a lower landmark;

providing a detection region based on the anatomical landmarks received from the pair of detector devices the detection region defined between the upper landmark and the lower landmark of the sternum of the patient;

providing one or more lateral pathway boundaries relative to the desired catheter pathway within the body cavity of the patient's body in the representation of the anatomical landmarks, the one or more lateral pathway boundaries positioned within the detection region and extending between the upper landmark and the lower landmark;

determining a position of a location transmitter of the catheter relative to the pair of detector devices using information received from the detector devices;

displaying, on the display, the position of the location transmitter of the catheter relative to the desired catheter pathway;

determining if the position of the location transmitter of the catheter approaches, reaches, and/or breaches any of the one or more lateral pathway boundaries;

determining if the position of the location transmitter of the catheter is within the detection region;

providing an indication when the location transmitter of the catheter approaches, reaches, and/or breaches any of the one or more lateral pathway boundaries within the detection region;

determining in real-time if the position of the location transmitter of the catheter passes below the xiphoid process, wherein the location transmitter is configured to extend beyond a width of the one or more lateral pathway boundaries when the catheter is below the xiphoid process, and wherein the indication is not provided when the location transmitter of the catheter is outside the detection region at the position below the xiphoid process and approaches, reaches, and/or breaches the width coinciding with any of the one or more lateral pathway boundaries.

13. The method of claim 12, wherein the step of determining if the position of the location transmitter of the catheter approaches, reaches, and/or breaches any of the one or more lateral pathway boundaries is conducted in real-time.

14. The method of claim 12, further comprising a step of adjusting the one or more lateral pathway boundaries using an input.

15. The method of claim 12, wherein the desired catheter pathway is defined along a midline of the patient, and wherein the one or more lateral pathway boundaries comprises at least one lateral boundary that is parallel to the desired catheter pathway.

16. The method of claim 15, wherein the one or more lateral pathway boundaries comprises a left lateral pathway boundary and/or a right lateral pathway boundary, wherein each of the left lateral pathway boundary and/or the right lateral pathway boundary are parallel to the desired catheter pathway.

17. The method of claim 12, further comprising determining a trajectory angle of a distal end of the catheter within the body cavity of the patient, and comparing the trajectory angle to a trajectory angle boundary defining a maximum acceptable angle of deviation from the desired catheter pathway.

18. The method of claim 12, wherein the step of providing the indication comprises displaying a visual indicator on the display, initiating an audible cue, and/or generating a haptic cue.

19. The method of claim 18, wherein a magnitude and/or frequency of the indication increases or decreases.

20. The method of claim 12, wherein the method further comprises steps of: establishing a maximum pathway boundary; and establishing a default initial pathway boundary.

21. A medical device placement configurable pathway deviation indication system comprising:

a catheter comprising a proximal end and a distal end, wherein the distal end is configured to be inserted into a desired catheter pathway within a body cavity of a patient;

a location transmitter configured to transmit a signal related to a position of the distal end of the catheter;

a pair of detector devices configured to receive information related to the patient's body and the location transmitter, wherein relative distances between each of the detector devices determine anatomical landmarks of the patient's body in real-time, wherein the information related to the anatomical landmarks comprises a suprasternal notch and a xiphoid process of the sternum of the patient, wherein the suprasternal notch defines an upper landmark and the xiphoid process defines a lower landmark;

a configurable pathway deviation indication system operatively coupled to the location transmitter and the at least one detector device, the configurable pathway deviation indication system comprising:

a display, a computing system comprising one or more processors and one or more non-transitory computer-readable media that collectively store instructions that, when executed by the one or more processors, cause the computing system to perform operations, the operations comprising:

providing a representation of anatomical landmarks of the patient's body and providing a detection region based on the anatomical landmarks received from the pair of detector devices the detection region defined between the upper landmark and the lower landmark of the sternum of the patient;

providing one or more lateral pathway boundaries relative to the desired catheter pathway in the representation of the anatomical landmarks, the one or more lateral pathway boundaries positioned within the detection region and extending between the upper landmark and the lower landmark;

displaying, on the display, the position of the location transmitter of the catheter relative to the desired catheter pathway;

determining in real-time if the position of the location transmitter of the catheter approaches, reaches, and/or breaches any of the one or more lateral pathway boundaries, determining in real-time if the position of the location transmitter of the catheter is within the detection region;

determining a trajectory angle of the distal end of the catheter within the body cavity of the patient;

comparing the trajectory angle to a trajectory angle boundary defining a maximum acceptable angle of deviation from the desired catheter pathway; and providing an indication when the location transmitter of the catheter approaches, reaches, and/or breaches any of the one or more lateral pathway boundaries within the detection region, determining in real-time if the position of the location transmitter of the catheter passes below the xiphoid process, wherein the location transmitter is configured to extend beyond a width of the one or more lateral pathway boundaries when the catheter is below the xiphoid process, and wherein the indication is not provided when the location transmitter of the catheter is outside the detection region at the position below the xiphoid process and approaches, reaches, and/or breaches the width coinciding with any of the one or more lateral pathway boundaries.

* * * * *